United States Patent [19]

Anis

[11] 4,166,293

[45] Sep. 4, 1979

[54] INTRAOCULAR LENS IMPLANT

[76] Inventor: Aziz Y. Anis, 1530 Janssen Dr., Lincoln, Nebr. 68520

[21] Appl. No.: 805,390

[22] Filed: Jun. 10, 1977

[51] Int. Cl.² ............................ A61F 1/16; A61F 1/24
[52] U.S. Cl. ......................................................... 3/13
[58] Field of Search ....................................... 3/13, 1

[56] References Cited

U.S. PATENT DOCUMENTS

| | | | |
|---|---|---|---|
| 3,971,073 | 7/1976 | Richards et al. | 3/13 |
| 3,986,214 | 10/1976 | Krasnov | 3/13 |
| 3,994,027 | 11/1976 | Jensen et al. | 3/13 |
| 4,012,823 | 3/1977 | Richards | 3/13 X |

Primary Examiner—Ronald L. Frinks
Attorney, Agent, or Firm—Henderson & Sturm

[57] ABSTRACT

An artificial intraocular lens implant for the anterior chamber of the eye after crystalline extraction is disclosed. The prosthetic lens includes a substantially light transparent disc having a central optical zone bounded at the rear thereof by three affixment points for three U-shaped loops of Nylon 66 or polypropylene material. The loops are arranged in a Y-shaped configuration such that two of the free legs, one from each adjacent loop, are connected at each affixment point, with the closed ends projecting outwardly and away from the plane of the disc. Additionally, a fourth U-shaped loop is affixed to the edge of the disc and projects away therefrom in a plane substantially parallel to that of the disc. The fourth loop is in substantial vertical alignment with one of the other three loops.

11 Claims, 5 Drawing Figures

INTRAOCULAR LENS IMPLANT

BACKGROUND OF THE INVENTION

This invention is directed generally to prosthetic devices, and particularly to such devices suitable for intraocular substitution.

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view in as much as it cannot properly refract incident light rays. Aphakic correction may be accomplished in three ways:
(1) thick eye glasses worn in front of the eye;
(2) contact lenses worn on the eye; or
(3) artificial intraocular lens implant within the eye. It is this latter procedure with which the instant invention is concerned.

The structure and procedure of installing an intraocular lens is very critical because the elements which make up the eye are extremely sensitive and subject to irrepairable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feet extending between the ciliary processes and the base of the iris. The lens proved positionally unstable and resulted in unsatisfactory amounts of irritation.

Logically, the anterior chamber of the eye was next investigated as a possible location for the implant. Here again, efforts proved unsatifactory because of irritation and positional instability.

Because of the structure of the eye, the implant must be either in the anterior or posterior chambers, thus, continued research is presently being directed toward both approaches.

The lens described in U.S. Pat. No. 3,673,616 comprises an anteriorly positioned lens with two supporting loops affixed thereto for arrangement behind the iris. A plurality of rods also project from the lens for arrangement in front of the iris. The iris expands and contracts between the rods and loops, but never completely expands beyond the space therebetween, thus holding the lens in position. The problems associated with a free-floating lens of this type are numerous. For example, the lens is not fixed in position and is therefore subject to a wide range of positional variation. Also, the iris is subjected in numerous locations to pressure necrosis caused by the rods rubbing against the iris.

Another device similar to that described immediately above is shown in U.S. Pat. No. 3,906,551. This particular prosthetic lens includes a pair of closely spaced apertures through which suturing thread is inserted for transversely fixing the lens in position.

U.S. Pat. No. 3,866,249 discloses a posteriorly positioned prosthetic lens which has a multiplicity of forwardly projecting prongs. During surgical implantation, the prongs are extended through the iris to anchor the lens in position. While this arrangement certainly maintains positional integrity, it, too, has distinct disadvantages. The great number of prongs extending through and over the iris promote undesirable irritational characteristics, and the numerous fixation points also have a tendency to distort the iris by pulling on it in numerous directions.

Finally, attention is directed to the devices disclosed in U.S. Pat. Nos. 3,925,825; 3,913,148; and 3,922,728. Each of these patents teach a prosthetic lens structure which is, in one way or another, less than desirable in construction and use.

BRIEF SUMMARY OF THE INVENTION

It is an object of this invention to provide a prosthetic intraocular lens for obviating aphakia.

It is another object of this invention to provide a prosthetic intraocular lens for implantation into the anterior chamber of the eye.

It is another object of this invention to provide an intraocular lens implant that is durable of construction, inexpensive of manufacture and extremely effective in use.

It is another object of this invention to provide an intraocular lens implant which is affixed to the iris diaphragm by a transiridectomy micro staple at one location to insure positional integrity.

It is a further object of this invention to provide an intraocular lens implant which does not interfere with the normal expansion and contraction activities of the pupil.

It is another object of this invention to provide an intraocular lens implant which does not distort the pupil from its normally round condition as do lenses which have multiple fixation points.

It is a still further object of this invention to provide an intraocular lens which does not irritate the sensitive portions of the eye.

These, and other objects are obtained, according to the instant invention, by providing an artificial intraocular lens implant for the anterior chamber of the eye after crystalline extraction. The prosthetic lens includes a substantially light transparent disc having a central optical zone bounded at the rear thereof by three affixment points for three U-shaped loops of Nylon 66 or polypropylene. The loops are arranged in a Y-shaped configuration such that two of the three legs, one from each adjacent loop, are connected at each affixment point, with the closed ends projecting outwardly and away from the plane of the disc. Additionally, a fourth U-shaped loop is affixed to the edge of the disc and projects away therefrom in a plane substantially parallel to and in vertical alignment with one of the three loops.

BRIEF DESCRIPTION OF THE DRAWINGS

For a better understanding of the invention as well as other objects and further features thereof, reference is made to the following detailed disclosure of the invention taken in conjunction with the accompanying drawings wherein.

DESCRIPTION OF THE PREFERRED EMBODIMENTS

Figure 1:
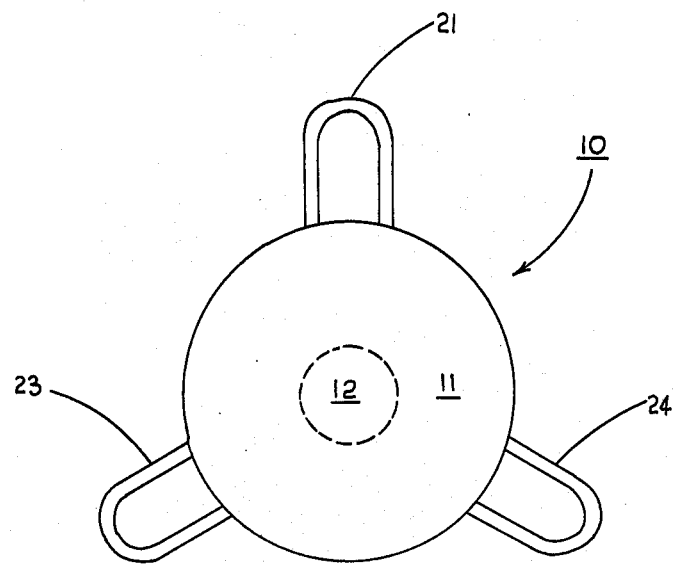
FIG. 1 is a partially schematic top plan view of the lens implant of the instant invention.
Figure 2:
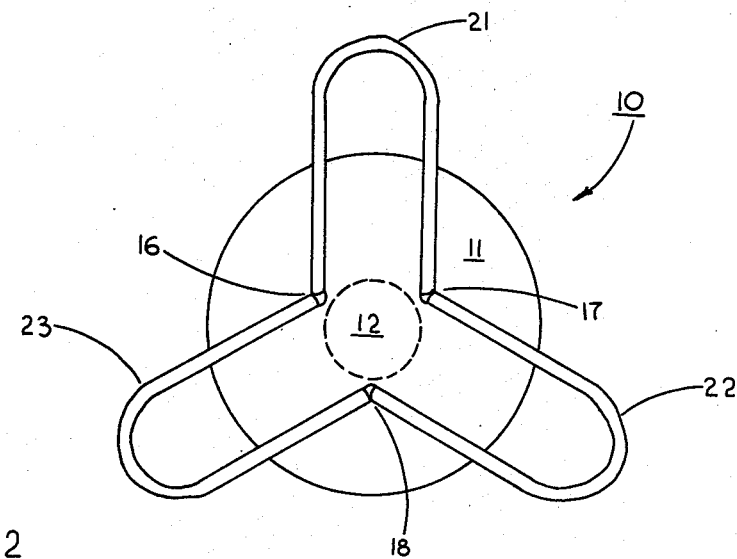
FIG. 2 is a partially schematic, bottom plan view of the lens implant of FIG. 1.
Figure 3:
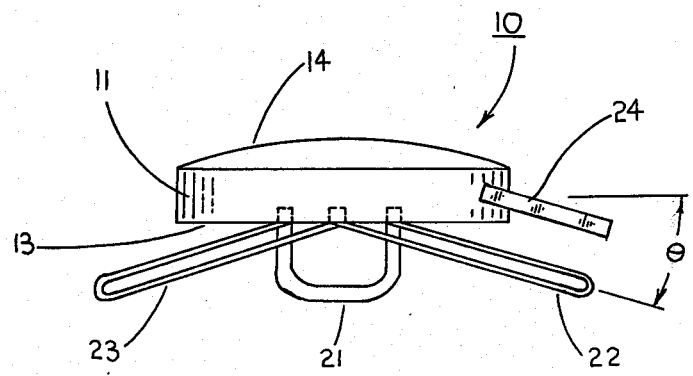
FIG. 3 is a partially schematic, side elevational view of the lens implant of FIGS. 1 and 2 showing the relationship among the various loops.

Referring now to FIGS. 1-3, the intraocular lens implant 10 of the instant invention is seen to include a substantially light transparent lens 11 with a central optical zone 12. The lens 11 may be of any suitable diameter, but generally falls somewhere in the range of about 5 mm (millimeters) to about 6 mm. It should be realized that the parameters and ranges given herein are merely exemplary and that actual optical and surgical variables are subjectively determined by the opthamologic surgeon in charge of the patient. The lens 11 may be made of any suitable material which may be made to exhibit the proper optical characteristics, and which is biologically inert. "Biologically inert" is a term used in the art to describe materials which are not susceptible to being absorbed by body fluids and which are capable of being tolerated by the human body when implanted. The most suitable material known for such lens implants is substantially polymethylmethacrylate, a compound commonly used in contact lens manufacture. Other suitable materials include quartz, opthalmic glass and polymeric materials.

The lens 11 may, of course, have generally any suitable cross-sectional configuration; however, it has been found that a flat rear surface 13 more easily accomodates an expanding and contracting pupil, and that the front surface 14 may be modified to provide the desired optical characteristics.

The optical zone 12 is shown in dotted lines only for the purposes of explanation, it being understood that the actual implant does not, in the preferred embodiment, exhibit any physical boundaries between zone 12 and the rest of lens 11. Optical zone 12 is that area of the lens in which the optical correction is made, and through which the vast majority of the incident light rays pass. Obviously, the diameter of the optical zone is another variable, usually staying within the range from about 2 mm to about 3 mm.

Three affixment points 16, 17 and 18 are positioned 120° apart around the center of the lens at the edge of the optical zone 12. U-shaped loops 21, 22 and 23 are positioned relative to each other such that the adjacent free ends of the adjacent loops are affixed to the lens 11 at the same affixment point. An additional loop 24 is affixed to the edge of lens 11, see FIG. 3, which is in substantial vertical alignment with and parallel to loop 22, so that the top and bottom plan views show only one of these loops. The loops can be made of any suitable material that is biologically inert and can be formed or drawn to a diameter of from about 0.10 mm to about 0.20 mm. For example, two polyamid synthetic fibers have been found particularly useful; one is identified as Prolene, a trade name of Ethicon Corporation, and the other is Supramid, a trade name of Jackson Company.

The three-point connection described immediately above is highly advantageous in aphakia correction. The number of elements which make up the implant is greatly reduced over the prior art, and thus potential irritation is minimized as are the possibilities of injury due to structure breakage. With the U-shaped holding elements affixed adjacent the optical zone, the iris is free to expand and contract to its full and natural limits without substantial contact with the implant.

Affixment of the various loops to the lens 11 may be accomplished in any suitable manner. It has, however, been found most advantageous to drill holes at each affixment point, insert the free ends of the loops and weld the connection with sonic techniques. For example, if a 0.15 mm diameter loop material is used, about a 0.3 mm diameter hole is drilled partway through the lens at each affixment point 16, 17 and 18. The ends of the loops are inserted, two in each hole, and a connection is made by sonic welding. Similarly, loop 24 is affixed by insertion of the free ends in a hole slightly larger than the 0.15 mm diameter loop material and welding them in place.

Of the various materials listed above for loop construction, it has been found that Prolene and Supramid are the most desirable. The angle $\theta$ shown in FIG. 3, should be approximately 10° to insure proper width between the lens and loops to accomodate the iris.

Figure 4:
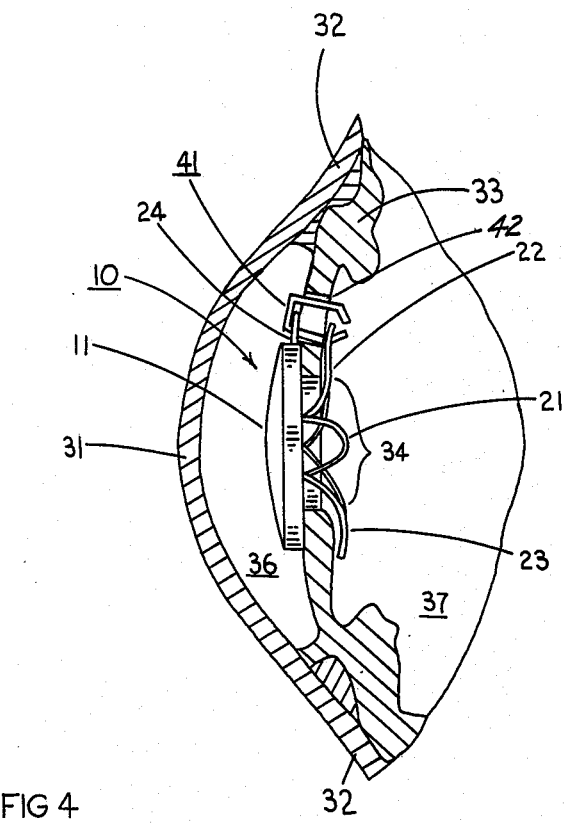
FIG. 4 is a sectional view of an eye showing an artificial lens implant according to the instant invention after implantation thereof.

Referring now to FIG. 4, the position and affixment of the lens implant 10 within the aphakic eye can be seen. The aphakic eye comprises a transparent cornea 31 which merges into an opaque protective covering 32 called the sclera. Behind the cornea 31 is the iris 33 which defines a central opening 34 known as the pupil. The iris 33 comprises a muscular diaphragm-like element capable of expansion and contraction to control the amount of light passed therethrough. The iris divides the internal chamber of the eye into two chambers, the anterior chamber 36 and the posterior chamber 37. The natural crystalline lens of the eye would be located in the posterior chamber 37 adjacent to pupil 34.

As can be clearly seen in this figure, the lens 11 is positioned within the anterior chamber 36 in contact with the forward portion of iris 33. The rear loops 21, 22 and 23 extend through the pupil and behind the iris 33. The loops alone will keep the lens 11 within the pupil, but will not guarantee total positional integrity. The loop 24 extends along the forward portion of the iris, substantially opposite loop 22. By projecting a micro-staple 41 through an iridectomy 42 to enclose the loops 22 and 24 the position of the lens will be made stable. More specifically, the lens will be fixed relative to the iris and will not drop out or rotate to any appreciable extent and, at the same time, the loops will maintain the lens over the pupil as the iris expands and contracts.

Figure 5:
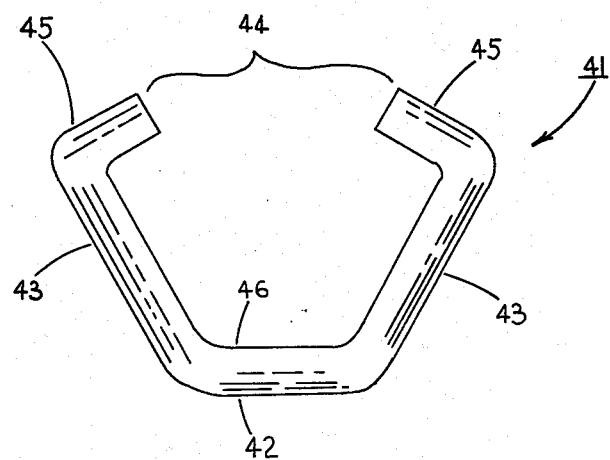
FIG. 5 is a partially schematic view of a micro-staple used to affix the lens of the instant invention in position.

The micro-staple 41, best seen in FIG. 5, is more completely described in co-pending United States Patent Application Ser. No. 805,265 entitled "METHOD AND APPARATUS FOR IMPLANTING AN INTRAOCULAR LENS," filed on the same day as the instant application in the name of the same inventor. Generally, the staple is made of biologically inert material of about 0.15 mm diameter, with a bottom of about 0.3 mm, sides 43 of about 0.75 mm and legs 45 of about 0.15 mm and an opening 44 of about 0.44 mm. Of course, the fixation step is completed by closing the opening 44 after insertion.

It will be understood that various changes in the details, materials, steps and arrangements of parts, which have herein been described and illustrated in order to explain the nature of the invention, will occur to and may be made by those skilled in the art upon a reading of this disclosure within the principles and scope of the invention.

I claim:

1. A biologically inert artificial intraocular lens implant for aphakic correction comprising:
    (a) a lens having a front face, a rear face and a outer peripheral edge;
    (b) only four holding members attached to said lens including, a first, second and third U-shaped holding member, each said holding member having a looped portion between two free ends, each said holding member secured at said free ends to said rear face, with the free ends of adjacent loops disposed adjacent each other and with said loop portions extending generally radially of said lens and equally spaced from each other;
    (c) a fourth U-shaped holding member having a looped portion between two free ends, said fourth member secured to said peripheral edge in vertical alignment with said first U-shaped member and generally parallel to said first U-shaped member.

2. A biologically inert artifical intraocular lens implant for aphakic correction comprising:
    (a) a lens having a front face, a substantially flat rear face and an outer peripheral edge;
    (b) said rear face of said lens further including first, second and third holes therein extending partway through said lens toward said front face, said holes being equally spaced from the center of the lens and about 120° apart;
    (c) first, second and third U-shaped holding members, each said holding member including a looped portion between first and second free ends, the said free ends of said holding members positioned in and fixedly secured to said first, second and third holes such that two of said free ends are in each hole, one from each adjacent holding member;
    (d) said outer edge of said lens further including fourth and fifth holes therein extending partway into said lens; and
    (e) a fourth U-shaped holding member including a looped portion between first and second free ends, the said free ends of said fourth holding member positioned in and fixedly secured to said fourth and fifth holes, respectively, said fourth and fifth holes being positioned relative to said first and second holes such that said fourth U-shaped holding member is generally parallel to and in vertical alignment with said first U-shaped holding member.

3. The lens implant of claim 2 wherein said first, second and third holes partially define a three-dimensional circular optical zone about and through the center of said lens.

4. The lens implant of claim 3 wherein at least said optical zone is of such a nature as to modify light waves passing therethrough.

5. The lens implant of claim 4 wherein the angle between the horizontal plane of said rear flat face and the plane of the U-shaped holding member having its first free end in said first hole and its second free end in said second hole is approximately 10°.

6. The lens implant of claim 4 wherein said first, second, third and fourth U-shaped holding members comprise a synthetic fiber.

7. The lens implant of claim 6 wherein the diameter of said synthetic fiber is in the range of from about 0.10 mm to about 0.20 mm.

8. The lens implant of claim 7 wherein the diameter of said first, second and third holes is about 0.3 mm.

9. The lens implant of claim 4 wherein the diameter of said lens is within the range of from about 5 mm to about 6 mm.

10. The lens implant of claim 7 wherein said lens comprises polymethylmethacrylate.

11. The lens implant of claim 10 wherein the diameter of said optical zone is within the range of from about 2 mm to about 3 mm.

* * * * *